United States Patent [19]

Lipps et al.

[11] Patent Number: 5,648,339

[45] Date of Patent: Jul. 15, 1997

[54] HERPOXIN: HERPES VIRUS INHIBITOR AND METHOD

[76] Inventors: Binie V. Lipps; Frederick W. Lipps, both of 4509 Mimosa Dr., Bellaire, Tex. 77401

[21] Appl. No.: 280,157

[22] Filed: Jul. 25, 1994

[51] Int. Cl.⁶ .......................... A61K 38/16; A61K 38/17; A61K 35/58
[52] U.S. Cl. ................... 514/21; 514/2; 514/12; 530/350; 530/856
[58] Field of Search .................. 530/350, 352, 530/856; 514/21, 2, 12

[56] References Cited

PUBLICATIONS

Joubert J. and Taljaard, N: "Purification, Some Properties and Amino–Acid Sequences of Two Phospolipases A (CM–II and CM–III) from *Naja naja* kaouthia Venom", Eur. J. Biochem., 112, pp. 493–499 (1980).

Richter "Clinical Immunology" pp. 25–29, 74–77, 1982, Williams & Wilkens, Baltimore.

*Primary Examiner*—Ponnathapura Achutamurthy
*Attorney, Agent, or Firm*—John R. Casperson

[57] ABSTRACT

Herpoxin, herpes virus inhibitor consists of two proteins isolated from snake venom of Naja n. kaouthia, which separately and together inhibit the replication of herpes simplex viruses type 1 and type 2 in cell cultures. Herpoxin is characterized as a purified component of snake venom, of the phospholipase $A_2$ (PhA2) enzyme family, which inhibits production of the typical cytopathogenic effects (CPE) produced by herpes viruses type 1 and type 2. Herpoxin consists of two peptides Herp-A and Herp-B having molecular weights 14,000 and 15,000 daltons, respectively, as revealed by gel electrophoresis. The partial sequence for the first fifteen N-terminal amino acids of both Herp-A and Herp-B is: Asn-Leu-Tyr-Gln-Phe-Lys-Asn-Met-Ile-Gln-Cys-Thr-Val-Pro-Asn, which will be referred to as SEQ ID No: 1. The known partial sequences for Herp-A and Herp-B proteins are identical and are typical of phospholipases. However, Herp-A and Herp-B are antigenically distinct. Herpoxin is claimed for its method of purification and as a treatment for herpes virus type 1 and type 2 induced oral and genital lesions and other infections. Herpoxin is further claimed as a therapeutic agent for non invasive topical application to treat other viral infections such as: herpes zoster, Kaposi sarcoma in AIDS patents, eczema, etc. It is also an object of this invention to provide Herpoxin as a composition for the treatment of skin infections induced by other microbial agents.

1 Claim, 3 Drawing Sheets

Well 1     markers
Well 2     Herp-A    14,000
Well 3     Herp-B    15,000

HERPOXIN: HERPES VIRUS INHIBITOR AND METHOD

FIELD OF THE INVENTION

The present invention relates to the discovery of the composition comprising Herpoxin as a herpes virus inhibitor, and its method of isolation from snake venom. Said composition of herpes virus inhibitor consists of two closely related peptides having approximate molecular weights 14,000 and 15,000 daltons.

BACKGROUND OF THE INVENTION

Snake venom is complex mixture of many substances with a wide spectrum of biological activities. Snake venom is a store house for numerous bioreactive components, such as toxins, enzymes, hormones and growth factors. Snake venom derived proteins have importance in medicine, pharmacology and various diagnostic procedures. The publication "Medical Use of Snake Venoms" by Kurt Stocker (1) reveals the state of the art.

The pioneering work of Sanders et al. (2) in the early fifties was the earliest reported study on the interaction of snake venom toxins and viruses. In 1958 the same authors (3) studied an antiviral effect of a snake venom neurotoxin in cell cultures and in animals. They demonstrated the inhibition of Semiliki Forest virus induced plaque formation by purified cobra venom neurotoxins. In 1977 the same authors (4) observed that venom neurotoxin interfered with the human strains of Poliomyelitis (Brunhild and Lansing) in Rhesus monkeys even after being chemically converted to a neurotoxoid.

In 1960 Anderson and Ada (5) observed that 100 µg/ml of purified phospholipase $A_2$ ($PhA_2$) from Pseudechis porphyriacus venom rapidly decreased the infectivity titer of Murray encephalitis virus. In the following year, similar observations were reported by Dayton (6) for Rous Sarcoma and MH2 tumor viruses. Venom derived phospholipase $A_2$ (enzyme name, phospatide acyl hydrolase) has several laboratory applications based on its ability to hydrolyze the acyl group on typical phoslipids of a cell membrane. However, phospholipase $A_2$ from various snake species differs substancially in molecular weight and activity.

Newcastle disease virus contains a "fusion factor" which causes animal cells to fuse. In 1967 Kohn (7) observed that this fusion was blocked by $PhA_2$ purified from Hydrophis haemachatus and Vipera palestinae venoms, although the hemagglutin, hemolysin and neuraminidase properties of the virus were not affected. Furthermore, in 1974 Wallstrom et al. (8) reported that $PhA_2$ from Naja nigricolis venom partially disrupted the envelop of influenza virus.

It is clear from the literature that snake venom proteins have been tested for their antiviral properties. Beginning two decades ago, venoms were tested on a limited scale but only for a few viruses, which were mostly RNA viruses. Furthermore, phospholipase $A_2$ from various species of snake venoms have shown antiviral activity on RNA viruses. The presence of numerous different proteins in typical snake venom suggests that there may also be antiviral factors for DNA viruses, specifically for herpes viruses. According to Meier (10), "Very interesting substances in snake venoms are waiting to be discovered".

Herpes simplex viruses type 1 and type 2 are double stranded DNA viruses. The clinical entities attributable to herpes virus type 1 include the following. (1) Acute herpetic gingivostomatitis which occurs mostly in small children. (2) Eczema herpeticum—Kaposi's varicelliform eruption. In this illness, there may be extensive vesiculation of the skin over much of the body and high fever. In rare instances the illness may be fatal. (3) Keratoconjunctivitis infection of eye. With recurrent infection there may be progressive involvement of the corneal stroma with permanent opacification and blindness. (4) Herpes encephalitis—carries a high mortality rate and survivers often have residual neurologic defects. (5) Herpes labialis—cold sores is the most common recurrent disease in the form of oral lesions.

Herpes virus type 2 is implicated in the following: (1) Genital herpes herpes progenitalis is characterized by vesiculoulcerative lesions of the penis of the male or the cervix, vulva, vagina and perineum of the female. (2) Neonatal herpes-herpes type 2 may be transmitted to the newborn during birth by contact with herpetic lesions in the birth canal producing permanent brain damage.

Varicella—zoster virus is a double stranded DNA virus and is morphologically identical with herpes simplex viruses. Herpes zoster—commonly known as shingles is a sporadic incapacitating disease of adults, rare in children, which is characterized by an inflammatory reaction of the posterior nerve roots and ganglia, accompanied by the affected sensory nerves.

SUMMARY OF THE INVENTION

The composition comprising Herpoxin has been isolated as a mixture of two phospholipase proteins by fractionating Naja n. kaouthia venom using high pressure liquid chromatography (HPLC). The fractionation of venom yielded seven major fractions. After testing for antiviral activity against HSV-1 and HSV-2 using individual fractions, the activity was revealed in fractions 6 and 7, having molecular weights approximately 14,000 and 15000 daltons, which are designated as: Herp-A and Herp-B and collectively referred as: Herpoxin. Herpoxin proteins are a variety of $PhA_2$, which is non toxic to cells and selectively inhibits the CPE production by herpes viruses in cell cultures.

Unlike other infections microbes such as bacteria, fungi and molds, viruses contain either DNA, or RNA, and never both, as genetic material. Viruses are intracellular parasites, and therefore, can not reproduce in a cell free environment. Host cell machinery and bioproducts are used by viruses for reproduction. The host cell dies or ruptures as the result of virus infection, which is the cytopathic effect, i.e. CPE. During one cycle of virus replication, numerous viral particles are produced, unlike the binary fission phenomena in microbes containing both DNA and RNA. The numerous viral particles bud out from the single infected cell and spread infection to neighboring cells, causing destruction of many cells and eliciting the CPE effects which are observed under an optical microscope. Thus, CPE is a manifestation of viral infection rather than the virus itself which can only be seen under an electron microscope. Similarly, inhibition of CPE is evidence that the viral infection is no longer occurring, which is the desired outcome of a therapy for the infection.

The concentration of 5 µg/ml of the herpes virus inhibitor, Herpoxin, in the medium inhibits the CPE formation by HSV-1 and HSV-2 viruses in human Chang's liver and human embryonic cells. This illustrates that the absorbed virus is made incapable from replication, maturation and budding out, in the presence of 5 µg/ml of the inhibitor.

Herpoxin failed to inhibit the CPE formation by HSV-1 and HSV-2 viruses in non human monkey Vero cells.

However, after treating the Vero cells with the inhibitor for 24 hours, and then infecting with HSV-1 or HSV-2 viruses, the CPE formation of HSV-2 is inhibited, but not of HSV-1. This is a surprising, first time observation, indicating that perhaps the receptors for HSV-1 and HSV-2 infectivity on Vero cells are different. The receptors required for HSV-2 infection on Vero cells appear to be blocked by the inhibitor Herpoxin. HSV-1 and HSV-2 viruses differ from each other on molecular level, as the two viruses are genetically different. This is the first observation suggesting a difference in two viruses at the cellular level, which is revealed by the CPE through Herpoxin mediator.

The cell culture experiments prove that Herpoxin is a potent inhibitor of infections due to herpes viruses type 1 and type 2 and, therefore, will be effective to treat herpes zoster infection. Its topical use can be extended to treat various infections caused by other agents such as Kaposi sarcoma induced by opportunistic infection occurring with human immunodeficiency virus (HIV), a double stranded RNA virus, and bacterial and fungal infections.

DETAILED DESCRIPTION OF THE INVENTION

Figure 1:
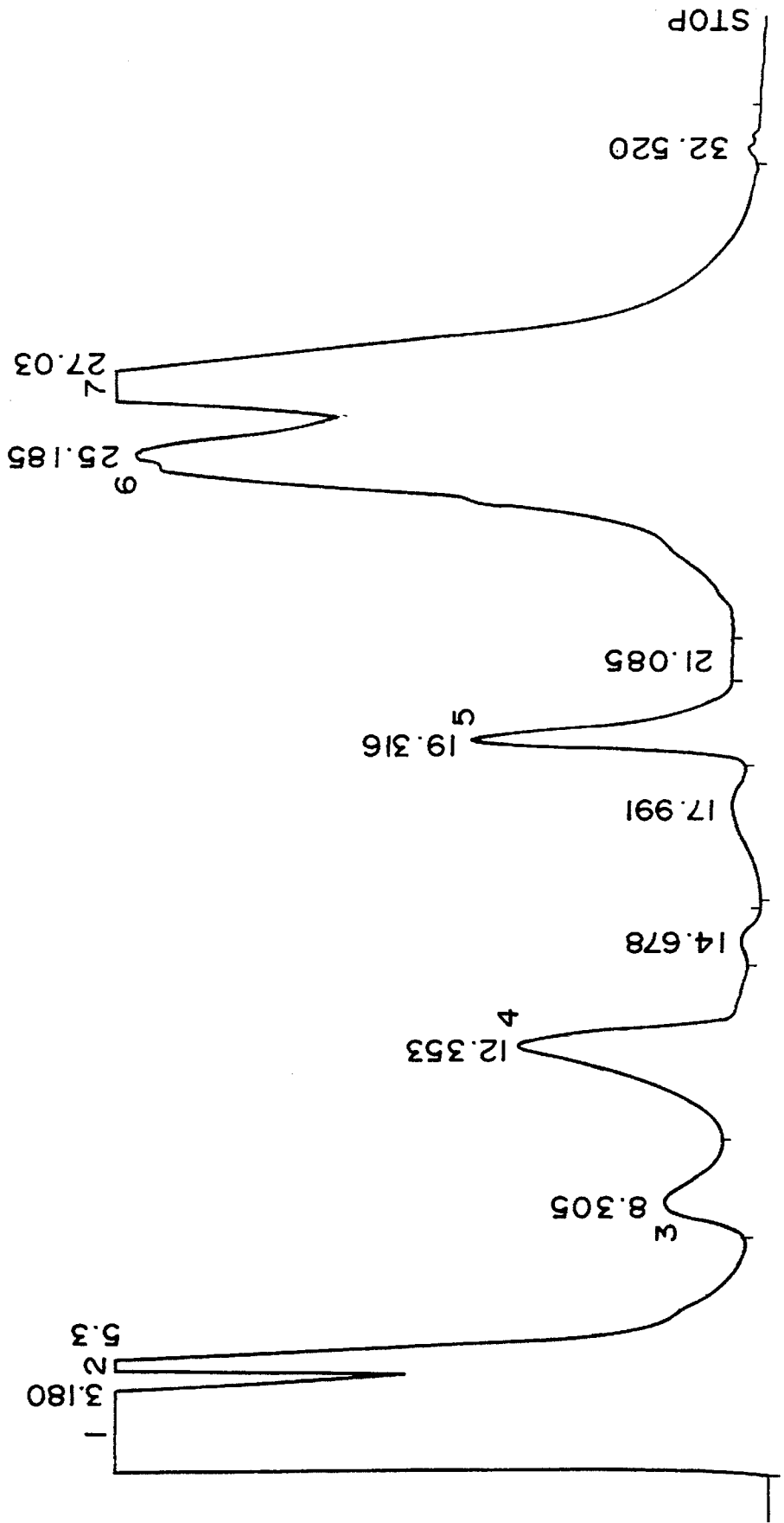
FIG. 1 is a high pressure liquid chromatography profile of Naja n. kaouthia venom using an ion exchange column. Peaks 6 and 7 represent Herp-A and Herp-B respectively having anti-viral activity.
Figure 2:
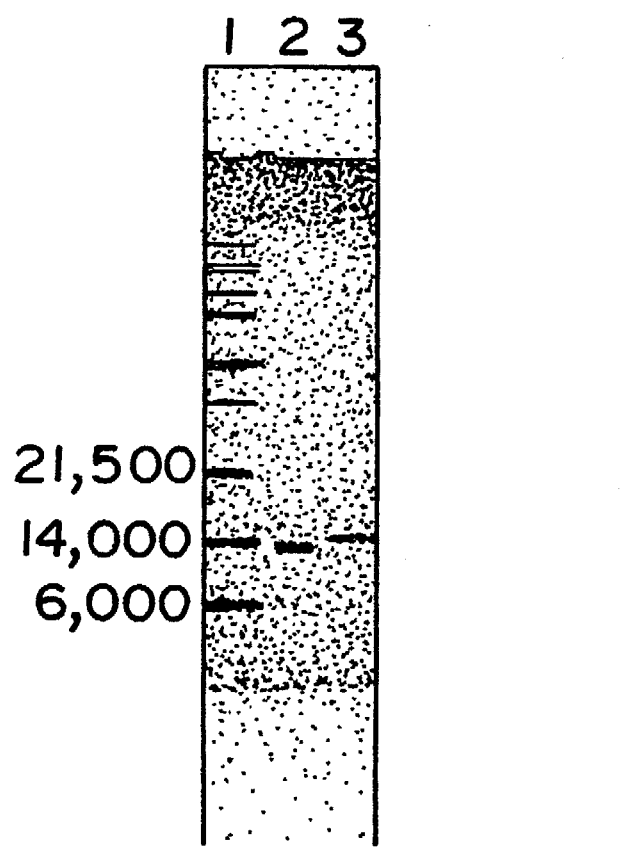
FIG. 2 is an electrophoresis profile of purified Herp-A and Herp-B on a 14% precast Novex® gel with markers, showing Herp-A in lane number two at approximately 14,000 Daltons and Herp-B in lane three at approximately 15,000 Daltons.
Figure 3:
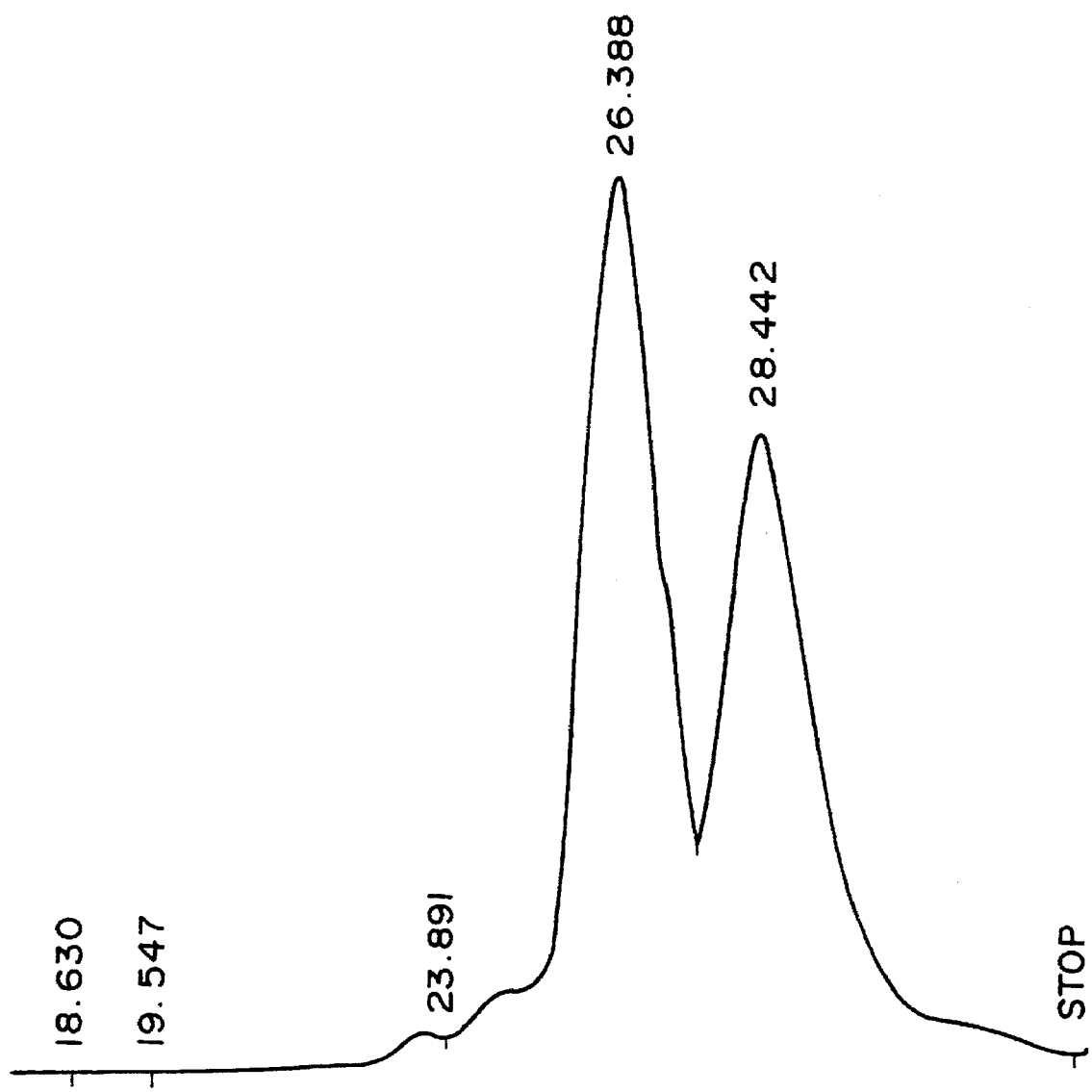
FIG. 3 is a high pressure liquid chromatography profile of concentrated fractions number 6 ad 7.

Herpoxin consists essentially of two phospholipase $A_2$ moieties (peptides), having slightly different ionic charge. The first fifteen N-terminal amino acids for both peptides is given by SEQ ID No: 1. It is known that many other phospholipase $A_2$ moieties do not share this partial sequence, and it is believed that any phospholipase having this amino acid sequence exhibits substantial utility as a herpes virus inhibitor, regardless whether it is synthesized or derived from natural sources. By the term "Herpoxin" or "herpes virus inhibitor", we mean a substance whose presence prevents infections produced by herpes viruses and its use can be extended to abrogate infections caused by other agents.

Preferably, the peptides of Herpoxin contain the first fifteen N-terminal amino acids which are similar to phospholipase $A_2$. Furthermore, the peptides of Herpoxin have molecular weights about 14,000 and 15,000 daltons revealed by electrophoresis, which are in the range of various known phospholipase $A_2$ proteins. In addition, Herpoxin is water soluble and stable at 4° C. temperature for several weeks retaining its biological activity—i.e. inhibition of CPE produced by HSV-1 and HSV-2 viruses.

Herpoxin, may be obtained essentially as a fraction of venom from species of poisonous snakes. In this invention Herpoxin is obtained from the venom of a cobra snake, specifically, the Naja n. kaouthia species.

The active Herpoxin is obtained by separating protein fraction by high pressure liquid chromatography, using ion exchange column and gradient Trizma-HCl buffer at pH 7.3.

Fractionation of Venom:

The active Herpoxin, a phospholipase $A_2$, is preferably separated from fresh frozen venom, although lyophilized whole venom may also be used. The liquid venom is diluted 1:1 with 0.01M phosphate buffer saline (PBS) and preferably centrifuged to sediment insoluble debris, which can also be removed by filtration. Typically, 40 mg of diluted and centrifuged venom is loaded on a high pressure liquid chromatograph, from Toso Co. Japan using an ion exchange column from Polymer Laboratories UK, and maintained at 20° C. temperature. A plurality of fractions elute according to relative ionic charge, preferably, using gradient Trizma-HCl buffer at pH 7.3. The Toso high pressure liquid chromatograph automatically mixes 1.0 molar Trizma-HCl buffer with water to yield gradient Trizma-HCl buffer in the range from 0.01 molar to 1.0 molar. Any suitable gradient buffer may be used and the Trizma-HCl buffer can have pH in the range 6.0 to 8.0.

The venom of Naja n. kaouthia resolved into 7 major fractions by high pressure liquid chromatography (Drawing No. 1). Fractions 6 and 7 represent the anti-HSV activity seen in cell culture. The fractions containing antiviral peptides may be used in this form as a composition to abrogate CPE caused by herpes viruses, and to treat other infections, but these fractions can be further purified to 100% purity. Preferably, the antiviral active fractions 6 and 7 are concentrated and dialyzed simultaneously, using dialysis apparatus from Spectrum Co., to $\frac{1}{20}^{th}$ volume and further purified by high pressure liquid chromatography by second run under identical conditions of gradient buffer, temperature, etc. The second elution of the Herpoxin fractions 6 and 7 each resolved into one peak (Drawing No. 2). Material obtained from these peaks was sequenced for the first fifteen N-terminal amino acids and found to be similar to phospholipase $A_2$.

Initially, each major fraction was tested in Chang's liver cells infected with HSV-1 or HSV-2. The fractions 6 and 7 of Naja n. kaouthia venom having slightly different molecular weights, exhibited CPE inhibition for both type 1 and type 2 herpes viruses in human Chang's liver and human embryonic cells. The inhibition of CPE occurred when 5 µg/ml of Herpoxin was added after the viruses were absorbed.

Herpoxin is a potential therapeutic agent to treat herpes virus induced oral and genital lesions and herpes zoster (shingles). Its use may be extended to infections caused by DNA viruses, and the double stranded RNA viruses, such as HIV, with associated Kaposi sarcoma found in AIDS patients.

Screening of CPE inhibitory activity of the venom fractions:

HSV virus stock having an approximate titer of $10^8$ PFU/ml (plaque forming units/ml) was diluted 1:100 to infect monolayers of Chang's liver cells grown in a 24 well plate. The virus was allowed to absorb for 1 hour at 37° C. in a humid $CO_2$ incubator. After absorption the excess virus was removed and 1 ml of Dulbecco's Modified Eagle medium (DMEM) supplemented with 2% fetal bovine serum (FBS) was added to each well. The venom of Naja n. kaouthia yielded seven major fractions. Each fraction was tested at 10, 5, 2.5, 1.0 and 0.5 µg/ml. Cells infected with virus received PBS to serve as positive controls, for virus cytopathic effects (CPE).

The tests were read after 4 days. Fractions 6 and 7 designated as Herp-A and Herp-B inhibited CPE formation for both HSV-1 and HSV-2 viruses at concentration as low as 1 µg/ml, without being toxic to the uninfected cells at 10 µg/ml concentration. The infected cells formed some sort of aggregates but not CPE in presence of these components. On staining with vital stain tryphan blue, the cells in the aggregates were not dead. Their microscopic morphology looked similar to the uninfected cells.

Fractions 6 and 7 were concentrated using the Spectrum dialysis system. The concentrated fractions were refractionated on HPLC in order to obtain 100% purity (Drawing 2). The molecular weights of these fractions are approximately 14,000 and 15,000, respectively, determined by electrophoresis using the 14% precast gel from Novex Co. in comparison to markers for aprotinin at 6,000, tyrosine at 14,000 and trypsin inhibitor at 21,500 daltons. (Drawing 3) Because of their herpes virus inhibitory activity these fractions are called as Herp-A and Herp-B, or simply A and B. Inhibition of HSV-1 and HSV-2 viruses by Herp-A and Herp-B in Chang's liver cells:

The monolayer cells in a 24 well plate were infected with HSV-1 or HSV-2 at $10^{-2}$ to $10^{-6}$ dilutions. After an absorption period, the excess inoculum was removed and 1 ml of medium was added to each well. Herp-A, Herp-B, and an equal mixture of Herp-A and Herp-B were added in 5 µg/ml in concentration. The results were read after 4 days of incubation.

TABLE 1

The Test Results

| Virus | Additive | Virus Concentrations | | | | | Controls |
|---|---|---|---|---|---|---|---|
| | | $10^{-2}$ | $10^{-3}$ | $10^{-4}$ | $10^{-5}$ | $10^{-6}$ | No Virus |
| HSV-1 | PBS | CPE | CPE | CPE | +++ | + | PBS |
| | Herp-A | — | — | — | — | — | Herp-A |
| | Herp-B | — | — | — | — | — | Herp-B |
| | A + B | — | — | — | — | — | A + B |
| HSV-2 | PBS | CPE | CPE | CPE | CPE | ++ | PBS |
| | Herp-A | — | — | — | — | — | Herp-A |
| | Herp-B | — | — | — | — | — | Herp-B |
| | A + B | — | — | — | — | — | A + B |

CPE= ++++ => 100% infected cells;
+++ => 75% infected cells;
++ => 50% infected cells;
+ => 25% infected cells;
— => 0% infected cells The results in Table 1 show that in the presence of 5 µg/ml of Herp-A, or Herp-B or in the combination of Herp-A+Herp-B, the CPE formation by HSV-1 and HSV-2 is inhibited and with no effect on the uninfected controls cells. Similar experiments were performed in Vero cells infected with herpes viruses. No inhibition of CPE was observed by incorporating 5 µg/ml, or 10 µg/ml of Herp-A, Herp-B or the combination of A and B.

Vero cell membrane receptors for HSV-1 and HSV-2 are different:

Vero cell cultures were treated with Herp-A, Herp-B and the A+B combination at 5 µg/ml concentration for 24 hours. The treated cultures were then infected with HSV-1 or HSV-2 viruses. It was observed that the CPE of only HSV-2 was inhibited by this treatment. These experiments indicate that the Vero cell receptors for HSV-1 and HSV-2 infection are different. The receptors for HSV-2 infection were blocked by Herpoxin, thus inhibiting the CPE formation.

Herp-A and Herp-B are antigenically different:

Polyclonal antibodies were produced by immunizing ICR mice with Herp-A and Herp-B individually. Immuno diffusion technique revealed that Herp-A specifically reacted only with anti Herp-A and not with anti Herp-B. Similarly, Herp-B specifically reacted with anti Herp-B, and not with Herp-A. This illustrates that Herp-A and Herp-B are antigenically distinct proteins. Apparently, Herp-A and Herp-B are sufficiently different in structure and amino acid composition to produce different antibody responses. (Table 2)

Amino acid composition of Herp-A and Herp-B is given in table 2

TABLE 2

Composition of Herpoxin

| Amino acid | Mole % Herp-A | Mole % Herp-B |
|---|---|---|
| Aspartic acid | 11.67 | 13.525 |
| Glutamic acid | 6.24 | 4.785 |
| Serine | 5.805 | 4.995 |
| Glycine | 7.59 | 6.39 |
| Histidine | 1.03 | 0.97 |
| Arginine | 4.04 | 4.755 |
| Threonine | 5.905 | 5.485 |
| Alanine | 7.855 | 8.20 |
| Proline | 3.435 | 3.04 |
| Tyrosine | 6.345 | 6.11 |
| Valine | 3.91 | 3.215 |
| Methionine | 1.04 | 0.88 |
| Cysteine | 11.16 | 12.355 |
| Isoleucine | 2.855 | 3.685 |
| Leucine | 4.67 | 4.255 |
| Phenylalanine | 3.40 | 3.34 |
| Lysine | 12.05 | 14.015 |

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 15
        ( B ) TYPE: AMINO ACID
        ( C ) STRANDEDNESS: SINGLE
        ( D ) TOPOLOGY: LINEAR (ii) MOLECULE TYPE: PROTEIN IN SEQ ID NO: 1

(iii) HYPOTHETICAL:NO (iv) ANTI-SENSE: NO (v) FRAGMENT TYPE: N (vi) ORIGINAL SOURCE: SNAKE VENOM: SEQ ID NO: 1:
  (A) ORGANISM: NAJA N. KAOUTHIA
  (B) STRAIN: WILD
  (C) INDIVIDUAL ISOLATE: THAILAND WILD
  (D) DEVELOPMENTAL STAGE: ADULT
  (E) HAPLOTYPE:
  (F) TISSUE TYPE:
  (G) CELL TYPE:
  (H) CELL LINE:
  (I) ORGANELLE:

(vii) IMMEDIATE SOURCE: SNAKE VENOM SEQ ID NO: 1:
  (A) LIBRARY:
  (B) CLONE:

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:

(xi) SEQUENCE DESCRIPTION: SEQ ID NO: 1:

```
Asn Leu Tyr Gln Phe Lys Asn Met Ile Gln
                 5                   10
Cys Thr Val Pro Asn
                15
```

The forgoing description of the invention is illustrative and explanatory thereof, and will be understood by those practiced in the art. It is intended that all variations within the scope and spirit of the appended claims be embraced thereby.

REFERENCES CITED

1. Stocker, K. F., "Medical Use of Snake Venom Proteins", Edited by Kurt F. Stocker, CRC Press 1990.
2. Sanders, M.; Soret, M. G.; Akin, B. A. and Roisin, L., Science 127: 594 (1958)
3. Sanders, M.; Soret, M. G.; and Akin, B. A., Annals of NY Academy of Science 28: 1 (1953)
4. Miller, K. D.; Miller G. C.; Sanders, M and Fellowes, O. N., Biochim. et Biophys. Acta 496: 192 (1977)
5. Anderson, S. G. and Ada, G. L., Nature (Lond) 188: 876 (1960)
6. Drayton, H., Nature (Lond) 192: 896 (1961)
7. Kohn, A. and Klibansky, C., Virology 31: 385 (1967)
8. Wahlstrom, A., Toxicon 9: 45 (1960)
9. Furie, B.C.; Furie, B.; Gotlieb, A. J. and Williams, J., Biochim. Biophys. Acta 365: 121 (1976)
10. Meier, J., Venomous Snakes in Medical Use of Snake Venom Proteins, Edited by Kurt Stocker CRC Press 1990 page 25.

We claim:

1. A method for treating an infection selected from the group consisting of Herpes virus type 1, and Herpes virus type 2, said method comprising applying topically a Herpes virus inhibitor comprising a first peptide and a second peptide to an area affected by said infection, wherein said first peptide has a molecular weight of approximately 14,000 Daltons, and wherein said second peptide has a molecular weight of approximately 15,000 Daltons, each said first peptide and said second peptide having the first fifteen N-terminal amino acids given by SEQ ID No: 1, wherein each said peptide is in the phospholipase A2 enzyme family and each said peptide is obtained from snake venom from the species Naja n. kaouthia.

* * * * *